(12) United States Patent
Mosler et al.

(10) Patent No.: US 9,579,221 B2
(45) Date of Patent: *Feb. 28, 2017

(54) PASSIVE ORTHOPEDIC AID IN THE FORM OF A FOOT PROSTHESIS OR FOOT ORTHOSIS

(71) Applicant: Otto Bock HealthCare GmbH, Duderstadt (DE)

(72) Inventors: Lueder Mosler, Duderstadt (DE); Roland Pawlik, Vienna (AT); Joachim Schoerg, Guntramsdorf (AT); Sven Kaltenborn, Duderstadt (DE); Sven Zarling, Duderstadt (DE); Greg Schneider, Minneapolis, MN (US)

(73) Assignee: Otto Bock HealthCare GmbH, Duderstadt (DE)

( * ) Notice: Subject to any disclaimer, the term of this patent is extended or adjusted under 35 U.S.C. 154(b) by 93 days.

This patent is subject to a terminal disclaimer.

(21) Appl. No.: 14/450,249

(22) Filed: Aug. 3, 2014

(65) Prior Publication Data

US 2014/0336782 A1 Nov. 13, 2014

Related U.S. Application Data

(63) Continuation of application No. 12/365,920, filed on Feb. 5, 2009, now Pat. No. 8,828,095.

(30) Foreign Application Priority Data

Feb. 7, 2008 (DE) .................. 10 2008 008 281

(51) Int. Cl.
| | | |
|---|---|---|
| *A61F 2/76* | (2006.01) | |
| *A61F 2/74* | (2006.01) | |
| *A61F 2/66* | (2006.01) | |
| *A61F 5/01* | (2006.01) | |
| *A61F 2/68* | (2006.01) | |
| *A61F 2/50* | (2006.01) | |
| *A61F 2/70* | (2006.01) | |

(52) U.S. Cl.
CPC .............. *A61F 2/68* (2013.01); *A61F 2/6607* (2013.01); *A61F 5/0127* (2013.01);
(Continued)

(58) Field of Classification Search
CPC .......... A61F 2/66; A61F 2/6607; A61F 5/0127
See application file for complete search history.

(56) References Cited

U.S. PATENT DOCUMENTS

| 6,443,993 B1 | 9/2002 | Koniuk |
| 2002/0138153 A1 | 9/2002 | Koniuk |

(Continued)

FOREIGN PATENT DOCUMENTS

| EP | 1 570 817 | 9/2005 |
| EP | 603 09 685 | 9/2007 |

(Continued)

*Primary Examiner* — Marcia Watkins
(74) *Attorney, Agent, or Firm* — Whitham, Curtis & Cook, P.C.

(57) ABSTRACT

The invention relates to a passive orthopedic aid in the form of a foot prosthesis or foot orthosis, with a first part which is connected to a second part in a rotatable manner via a swivel joint, with a sensor arrangement for measuring parameters that provide indications of instantaneous operation requirements of the aid, with a control means which is connected to the control arrangement and is used to determine operation requirements and to generate corresponding control signals, with a controllable hydraulic damping arrangement with which a movement resistance acting on the rotation movement between the first part and the second part can be modified, and with a control means which converts the control signals of the processor arrangement and is used to control the damping arrangement. The foot prosthesis is characterized in that the damping arrangement is a dual-action hydraulic cylinder with two hydraulic chambers separated from each other by a piston, and in that the hydraulic chambers are connected via two connection lines which permit a flow of the hydraulic fluid only in mutually opposite directions and whose flow resistances can be adjusted by the control separately and via their own adjustment means each, in that the processor arrangement is configured to determine a current neutral point position from the measured parameters of the sensor arrangement, and in that the control signals for the flow resistances in the two connection lines are generated with respect to the neutral point position.

9 Claims, 3 Drawing Sheets

(52) U.S. Cl.
CPC .......... *A61F 2002/5006* (2013.01); *A61F 2002/5033* (2013.01); *A61F 2002/5035* (2013.01); *A61F 2002/5038* (2013.01); *A61F 2002/5072* (2013.01); *A61F 2002/6818* (2013.01); *A61F 2002/6854* (2013.01); *A61F 2002/704* (2013.01); *A61F 2002/74* (2013.01); *A61F 2002/745* (2013.01); *A61F 2002/748* (2013.01); *A61F 2002/764* (2013.01); *A61F 2002/7625* (2013.01); *A61F 2002/7645* (2013.01); *A61F 2005/0141* (2013.01); *A61F 2005/0144* (2013.01); *A61F 2005/0158* (2013.01); *A61F 2005/0169* (2013.01); *A61F 2005/0179* (2013.01)

(56) References Cited

U.S. PATENT DOCUMENTS

| | | |
|---|---|---|
| 2005/0192677 A1 | 9/2005 | Ragnarsdottir |
| 2005/0197717 A1 | 9/2005 | Ragnarsdttir et al. |
| 2006/0224247 A1 | 10/2006 | Clausen et al. |
| 2006/0235544 A1 | 10/2006 | Iversen et al. |
| 2007/0027555 A1 | 2/2007 | Palmer et al. |
| 2008/0262635 A1 | 10/2008 | Moser et al. |
| 2008/0288086 A1 | 11/2008 | Auberger et al. |
| 2009/0030530 A1 | 1/2009 | Martin |

FOREIGN PATENT DOCUMENTS

| | | |
|---|---|---|
| JP | 2005-087347 | 4/2005 |
| JP | 2007524483 | 8/2007 |
| WO | WO 03/086245 | 10/2003 |
| WO | WO 2006/000211 | 1/2006 |
| WO | WO 2006/112774 | 10/2006 |
| WO | WO 2008/103917 | 8/2008 |

PASSIVE ORTHOPEDIC AID IN THE FORM OF A FOOT PROSTHESIS OR FOOT ORTHOSIS

CROSS-REFERENCE TO RELATED APPLICATIONS

This application is a continuation application of U.S. Ser. No. 12/365,920 filed Feb. 5, 2009, now U.S. Pat. No. 8,828,095.

The invention relates to a passive orthopedic aid in the form of a foot prosthesis or foot orthosis, with a first part which is connected to a second part in a rotatable manner via a swivel joint, with a sensor arrangement for measuring parameters that provide indications of instantaneous operation or usage requirements of the aid, with a processor arrangement for determining the operation or usage requirements and for generating corresponding control signals, with a controllable hydraulic damping arrangement with which a movement resistance acting on the rotation movement between the first part and the second part can be modified, and with a control means which converts the control signals of the processor arrangement and is used to control the damping arrangement.

Orthopedic aids of this kind are known in particular as foot prostheses. The swivel joint is usually an ankle joint via which an attachment part for a below-knee prosthesis is connected to a foot part.

In a foot prosthesis known from US 2005/0197717 A1, the foot part has an elastic sole spring that extends along the length of the foot part. The damping effected by the elasticity of the sole spring in the stance phase of the gait cycle is in this case supplemented by an active adjustment of the angle of the foot part relative to the part for attachment to the lower leg. This permits adjustment to an inclined ground surface or to a modified height of the heel of a shoe that is being worn, the heel height being modified by suitable manual input into the control means. The actuator used is preferably a dual-action motor, particularly in the form of a double-screw motor. The use of a dual-action actuator requires a large amount of energy for the function of the prosthesis, such that it is necessary either to use a large-volume battery with a large storage capacity or to frequently recharge the battery.

A passive foot prosthesis of the type mentioned in the introduction is known from U.S. Pat. No. 6,443,993 B1 and from US 2002/0138153 A1. Between a foot part and an attachment part for a lower leg, damping cylinders are provided, one to the front of and one to the rear of the ankle joint, which damping cylinders function in a tandem arrangement and are connected to each other via a common connection line. When weight is placed on the heel, the rear cylinder is compressed, such that hydraulic fluid passes through the connection line into the front cylinder. The speed of flow of the hydraulic fluid through the connection line, and with it the damping of the corresponding compression movement on the heel, is adjusted by using a magneto-rheological fluid as the hydraulic fluid and by using a coil to build up a suitable magnetic field which modifies the viscosity of the magneto-rheological fluid. The sensors used are an absolute inclination sensor and a floor contact sensor. Provision is made to increase the damping in the stance phase of the gait cycle, for example when the inclination sensor detects that the plumb line has been crossed, in particular to switch from a first damping level to a second damping level. This permits a certain adjustment of the prosthesis to inclines of the ground surface and to different heights of heel.

The problem arising from the prior art is that although the control of a passive foot prosthesis or foot orthosis permits individual adjustments, it still has considerable shortcomings compared to the behavior of a natural healthy foot.

The object of the present invention is therefore to permit improved adaptation to the behavior of a natural foot, by means of a passive orthopedic aid in the form of a foot prosthesis or foot orthosis.

According to the invention, this object is achieved by a passive orthopedic aid in the form of a foot prosthesis or foot orthosis which is of the type mentioned in the introduction and is characterized in that the damping arrangement is a dual-action hydraulic cylinder with two hydraulic chambers separated from each other by a piston, in that the hydraulic chambers are connected via two connection lines which permit a flow of the hydraulic fluid only in mutually opposite directions and whose flow resistances can be adjusted by the control separately and via their own adjustment means each, in that the processor arrangement is configured to determine a current neutral point position from the measured parameters of the sensor arrangement, and in that the control signals for the flow resistances in at least one connection line are generated starting from the neutral point position.

The foot prosthesis or foot orthosis according to the invention thus comprises a dual-action hydraulic cylinder whose synchronously changing hydraulic chambers are connected to each other via two connection lines, both connection lines being provided with their own adjustment means for adjusting their flow resistances. The adjustment means can in particular be controllable valves whose cross section of flow can be modified, preferably steplessly. This arrangement makes it possible, during a gait cycle, for different flow resistances for the flow of hydraulic fluid in one direction and in the other to be obtained quickly and accurately. In addition, the use of dedicated adjustment means can ensure a continuous transition from the movement of the foot part in one direction to the other direction. To control the ankle joint, it is thus possible, for example, to achieve a controlled transition from plantar flexion to dorsiflexion when the weight changes from the heel to the front of the foot, while at the same time ensuring that, in the transition from the stance phase to the swing phase of the gait cycle when the weight is removed from the front of the foot, the dorsiflexion can be maintained for a certain time in order to allow the lifting of the front of the foot at the start of the swing phase to be maintained until the leg is swung through a middle position, as occurs with a natural healthy foot, in order to avoid the tips of the toes hitting the floor during swing through.

According to the invention, the sensor arrangement and the processor arrangement are to be configured in such a way that a current neutral point position can be determined. A processor arrangement suitable for this purpose is composed, for example, of an ankle moment sensor and of an inclination sensor or absolute angle sensor, if the swivel joint performs the function of an ankle joint. In addition to this, an ankle angle sensor can preferably be provided. It is thus possible to determine a current dorsal limit by determining the absolute angle when passing the neutral point of the ankle moment in the stance phase of the gait cycle. In this way, the current inclination of the ground surface or the respective heel height can be taken into account in each gait cycle without time lag. Since the heel height and the inclination of the ground surface have the same influence in the measured signal, it is expedient to determine the constant influence of the heel height through corresponding evaluation of the signals in the stance phase of the gait cycle or during standing. As an alternative to this, the heel height can also be entered manually into the evaluation means.

In a preferred embodiment of the invention, the flow resistances in the two connection lines can be made so great that the swivel joint can be locked in position. The adjustment means can therefore be used to lock the swivel joint, such that no separate locking means is needed, for example in order to ensure a stable support by the prosthesis or orthosis when the person wearing the orthopedic aid is standing. The locked position can correspond to the determined neutral point position.

In a particularly preferred embodiment of the invention, the parts of the aid are mostly rigid. At least most of the movement within a movement cycle is controlled by the control of the flow resistances, without being influenced by material elasticities. It may at most be expedient to make use of a certain material elasticity when the heel is placed on the ground during walking.

With the orthopedic aid according to the invention, it is thus possible to determine a neutral point position of the rotation movement, starting from which the flow resistances for the first and second directions of movement of the swivel joint, in particular of the ankle joint, are determined. For a defined input requirement, for example during standing, the swivel joint is locked, preferably in the neutral point, by means of high movement resistances being set in both directions of movement. The movement cycle is in this case preferably a gait cycle.

In another preferred embodiment of the invention, the part attached to the swivel joint is a foot part, which is divided into a main foot part and a forefoot part, the forefoot part being connected to the main foot part via a hinge. The hydraulic cylinder can be hinged on the forefoot part, in order thereby to adjust the angle setting of the main foot part indirectly, namely via the forefoot part.

The invention is explained below in more detail on the basis of an exemplary embodiment illustrated in the drawing, in which FIG. 1 shows a schematic illustration of a first exemplary embodiment of a foot prosthesis according to the invention;

Figure 1:
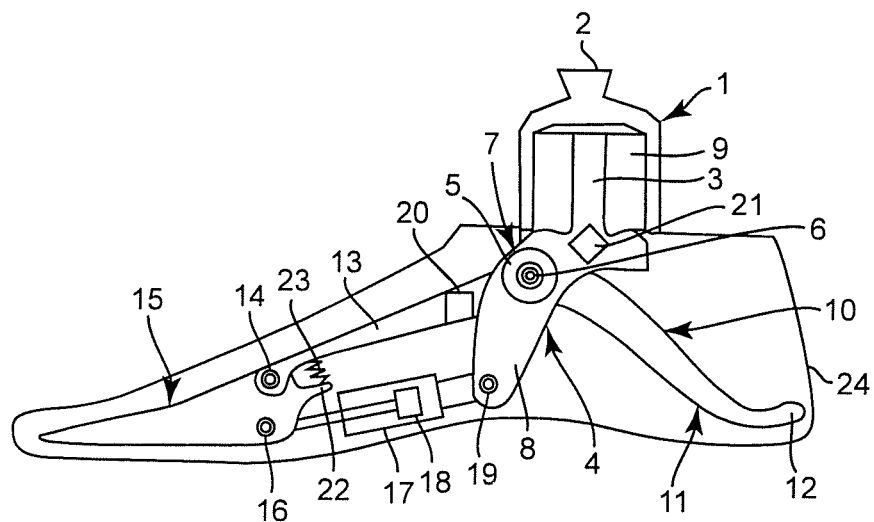

In the exemplary embodiment illustrated in FIG. 1, an attachment piece 1 is formed with an adjustment attachment 2 in the form of an upside-down pyramid frustum with four angled surfaces. The attachment piece 1 forms a pot which opens downward and into which an upwardly pointing web 3 of a two-armed lever 4 extends. The two-armed lever can rotate about a swivel joint 5, the axis of rotation 6 of which simultaneously forms the axis of an ankle joint of the artificial foot. The swivel joint 5 is provided with an angle sensor 7. The two-armed lever 4 has a rigid attachment 8 which extends downward.

The intermediate space formed by the web 3 in the downwardly open pot of the attachment piece 1 is filled by relatively stiff elastic material 9, such that the movement of the attachment piece 1 is transferred to the movement of the web 3 of the two-armed lever 4 with only slight damping. Accordingly, the attachment 8 moves like the attachment piece 1, but in a slightly damped fashion due to the elastic material 9.

The swivel joint 5 forming the ankle joint furthermore carries a main foot part 10, which likewise extends a two-armed lever into the heel region of the foot with a rear lever arm 11, where the rear lever arm 11, which runs obliquely rearward and downward, is provided with an end 12 that is rounded approximately horizontally.

The main foot part has a front lever arm 13 which extends toward the front from the ankle joint 5 and which extends forward, slightly obliquely downward, in an almost straight line from the ankle joint 5 so that the main foot part 10 is designed such that it arches upward toward the ankle joint 5 and drops obliquely, from the ankle joint 5, into the heel region toward the rear and into a forefoot region toward the front, with the oblique drop into the heel region being steeper than the oblique drop into the forefoot region.

The front lever arm 13 of the main foot part 10 ends at the beginning of the forefoot region and carries a swivel joint 14 at that location, by means of which a forefoot part 15 replicating a toe region is rotatably hinged on the front lever arm 13 of the main foot part. The swivel joint 14 has an axis of rotation which runs horizontally, parallel to the axis of rotation 6 of the ankle joint 5. Since the forefoot part 15 mimics the toe region of a natural foot, its design toward the front is triangular and tapers off. Below the swivel joint 14 there is a further swivel joint 16 on the forefoot part 15, by means of which a piston rod of a piston 18 of a hydraulic cylinder 17 is hinged on the forefoot part 15. The hydraulic cylinder 17 is rotatably hinged on the free end of the downwardly extending attachment 8 of the two-armed lever 4 by means of a swivel joint 19, such that the swivel joint 19 is arranged below the ankle joint 5 and is slightly offset toward the front (in the direction of the forefoot region 15) with respect to said ankle joint.

The ankle joint 5 comprises the angle sensor 7 for measuring the ankle angle, that is to say the angle between the web 3 (which is arranged flush with the lower leg) and the front lever arm 13 of the main foot part 10.

The front lever arm 13 of the main foot part 10 also carries an inclination sensor 20 which determines the inclination relative to the gravitational force (relative to the plumb line). Such inclination sensors 20, which determine an absolute inclination angle relative to the gravitational acceleration, are known as acceleration sensor arrangements with or without a gyroscope.

The two-armed lever 4 comprises an ankle moment sensor 21 which is flush with the adjustment attachment 2, i.e. flush with the (artificial) lower leg of the patient, and which measures the torque acting at said location.

At its rear end, the forefoot part 15 is provided with a bearing attachment 22 used to hold a spring 23 which can be loaded with tension and pressure and which is supported at its other end on the front lever arm 13 of the main foot part 10. The spring 23 effects a return of the forefoot part 15 after dorsiflexion, the return velocity being determined by the hydraulic cylinder 17.

The hydraulic cylinder 17 is designed as a passive actuator, in which the hydraulic flow effected by the piston 18 is controlled by valves (not illustrated), with it being possible to not only switch the valves on and off, but also to control them to have a defined flow rate.

Figure 2:
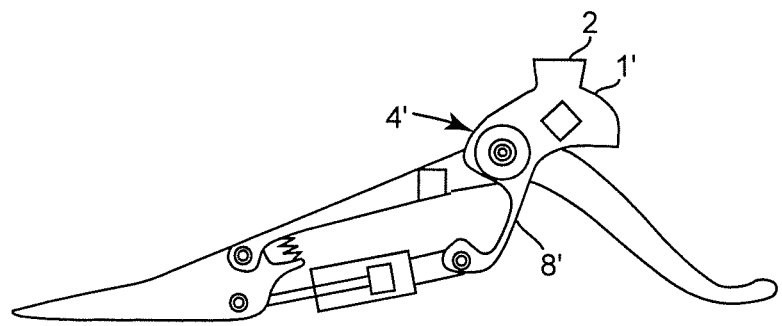
FIG. 2 shows a schematic illustration of a second exemplary embodiment of a foot prosthesis according to the invention.

The embodiment illustrated in FIG. 2 substantially corresponds to the embodiment in accordance with FIG. 1. One difference lies in the fact that the attachment piece 1' with the adjustment attachment 2 is designed integrally, so that elasticity formed by the elastic material 9 is no longer present. Instead, the downwardly extending attachment 8' of the two-armed lever 4' is designed with a thinning of the material so that the free end of the attachment, which carries the swivel joint 19, is arranged in a resilient manner with respect to the remaining material of the two-armed lever 4'.

It goes without saying that the artificial foot in accordance with the second embodiment also has a cosmetic cover 24, just like the first embodiment. However, this cosmetic cover 24 is not illustrated again in the second and third embodiments.

Figure 3:
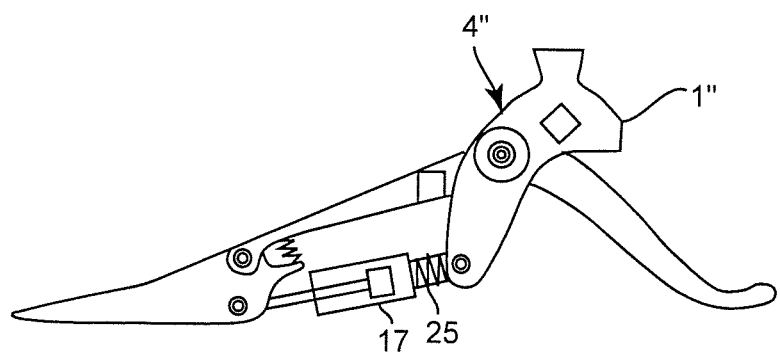
FIG. 3 shows a schematic illustration of a third exemplary embodiment of a foot prosthesis according to the invention.

In the case of the third embodiment of the artificial foot, illustrated in FIG. 3, the two-armed lever 4" and the adjustment attachment 2 are also designed integrally. The downwardly extending attachment 8 of the two-armed lever 4" is also rigid, just like in the first embodiment. Instead, the hydraulic cylinder 17 is elastically connected to the downwardly extending attachment 8 of the two-armed lever 4" by means of a coil spring 25. This permits elasticity in series with the action of the hydraulic cylinder 17, which elasticity is implemented by the elastic material 9 in the embodiment illustrated in FIG. 1 and by the resilient attachment 8' in the embodiment illustrated in FIG. 2. All other parts of the third embodiment correspond to those of the first embodiment.

Figure 4:
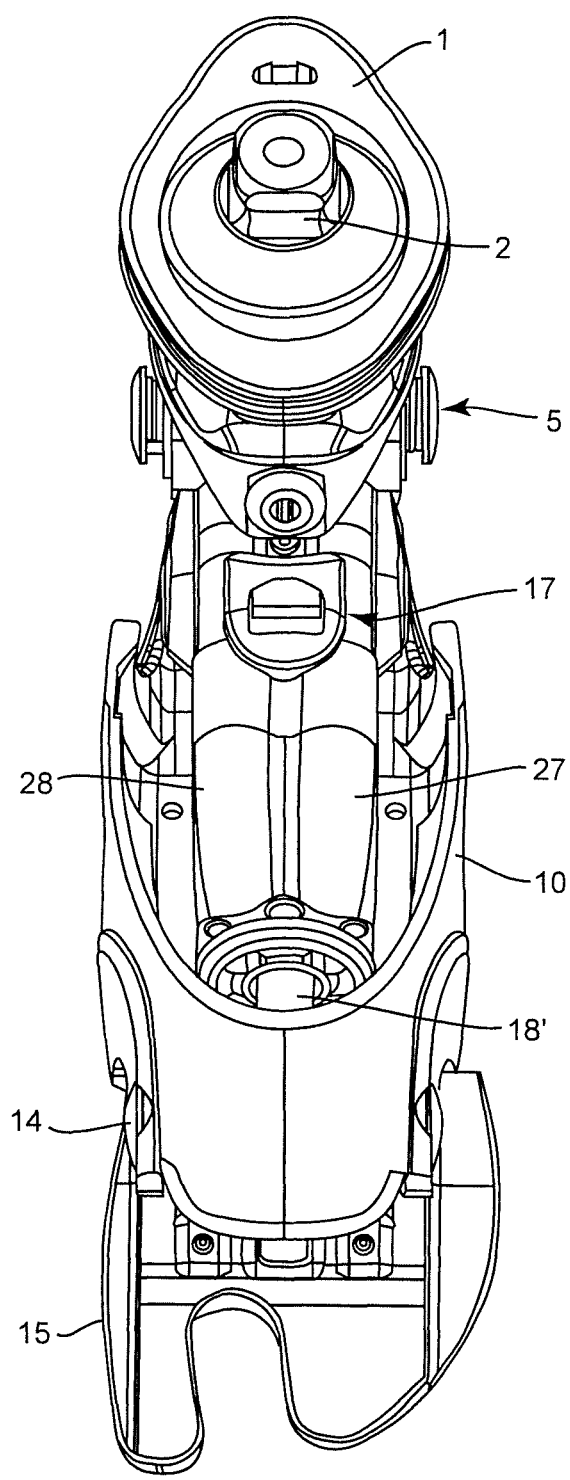
FIG. 4 shows a plan view of a structurally detailed further embodiment of a foot prosthesis according to the invention.
Figure 5:
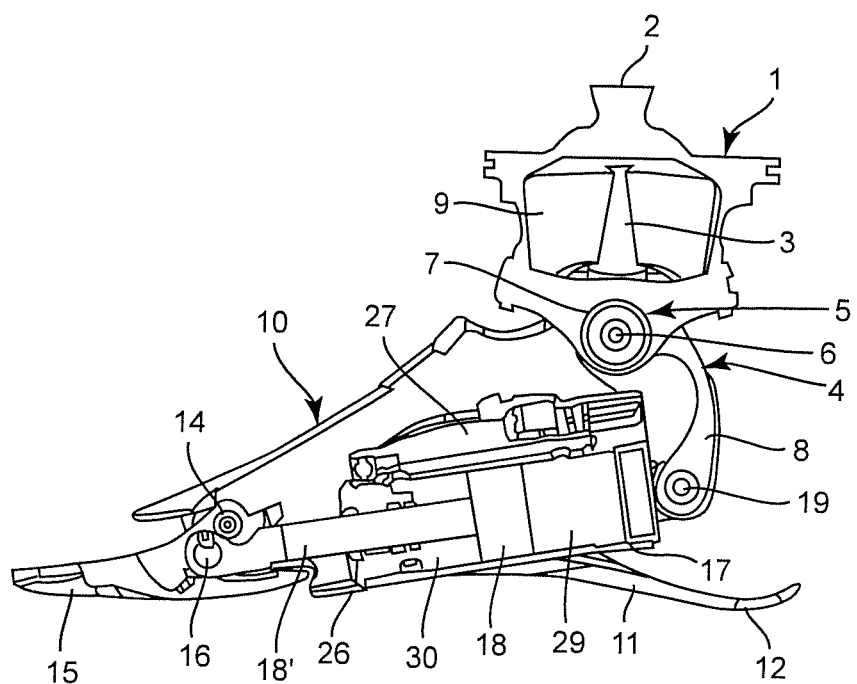
FIG. 5 shows a vertical section parallel to the sagittal plane through the foot prosthesis in accordance with FIG. 4.

The exemplary embodiment illustrated in FIGS. 4 and 5 reveals the attachment piece 1 with the pyramidal adjustment attachment 2. The elastic material 9 located in the attachment piece 1 interacts in a damping fashion with the upwardly extending web 3 of the two-armed lever 4. In this exemplary embodiment, the downwardly extending attachment 8 of the two-armed lever 4 runs behind the ankle joint 5 in the walking direction and is, at that location, hinged to the hydraulic cylinder 17 via the swivel joint 19. The piston 18 moves in the hydraulic cylinder 17 such that it can be displaced longitudinally and can be led out via a bearing 26, located in the hydraulic cylinder 17, and connected to the further swivel joint 16 of the forefoot part 15. The ankle joint 5 furthermore serves to mount the main foot part 10 which in this case is in the foam of a rigid housing and comprises an elastic lever 11 which is directed toward the rear and serves as a heel lever. Hence, the foot part 10 and the heel lever 11 can together be pivoted around the ankle joint 5 and relative to the attachment piece 1 and the two-armed lever 4. The pivot movement between the attachment piece 1 and the foot part 10 is controlled and damped by the two-armed lever 4 and the hydraulic cylinder 17. Hinging the piston rod 18' of the piston 18 to the forefoot part 15 in this case only effects an additional control of the forefoot part 15 forming the toe plate and this, however, only slightly modifies the control of the main foot part 10 since the further swivel joint 16 is arranged in the direct vicinity of the swivel joint 14, between the forefoot part 15 and the main foot part 10. The hydraulic cylinder 17 is provided with two control valves 27, 28 which are arranged on the top side of the hydraulic cylinder 17. The control valves 27, 28 are connected to the chambers 29, 30 of the hydraulic cylinder 17 on both sides of the piston 18, with check valves (not illustrated) ensuring that the hydraulic fluid can only flow from the lower chamber 29 to the front chamber 30 through the first control valve 27, and this permits the insertion movement of the piston 18 into the hydraulic cylinder 17, which corresponds to plantar flexion of the main foot part 10 with respect to the attachment piece 1. The other control cylinder 28 only permits the hydraulic flow from the front chamber 30 to the back chamber 29 by means of check valves; as a result of this, the piston 18 can be pulled out of the hydraulic cylinder 17, i.e. the distance between the swivel joints 19, 16 is increased. This corresponds to dorsiflexion between the attachment piece 1 and the main foot part 10. At the same time, the displacement of the swivel joint 16 with respect to the swivel joint 14 effects a lifting of the forefoot part 15 toward the front.

In the illustrated embodiments, the artificial foot has the same method of operation. The sensor arrangement for measuring the ankle angle, the ankle moment and the absolute inclination angle makes it possible to determine the relevant functional states of the artificial foot and distinguish between them, the signal of the ankle-angle sensor being evaluated to determine, on the one hand, the ankle angle (between attachment piece 1, 1', 1" and the main foot part 10) and, on the other hand, the respective ankle angular velocity.

By way of example, it is possible to detect whether the artificial foot is used for walking or standing by determining the ankle angular velocity at the zero crossing of the ankle moment. If the ankle angular velocity is below a threshold during the zero crossing of the ankle moment, this is recognized as "standing" and the actuator in the form of the hydraulic cylinder 17 is set to have a high resistance by means of the valves such that a dorsal stop can be formed by said actuator.

A declining inclination or the heel height is determined by means of the inclination sensor 20 in the metatarsal region of the main foot part 10 during the zero crossing of the ankle moment.

If walking in the plane is detected, then the valve which is responsible for the plantar flexion of the foot is left in a half-open setting while the valve which determines the dorsiflexion is closed with increasing ankle angle to form a dorsal stop.

If uphill walking is detected, an increased dorsiflexion of the forefoot part 15 is permitted.

If the heel impact after the swing phase and at the beginning of the stance phase is detected during walking by a negative ankle moment in particular, then the valve for the plantar flexion is controlled in such a manner that it closes with an increasing ankle angle in the direction of plantar flexion and hence forms a stop for the plantar flexion.

If a toe push-off is detected at the end of the stance phase (decreasing ankle moment in the case of an enlarged ankle angle), the valve for the dorsiflexion is completely opened after a dead time in order to initiate the lifting of the forefoot part (lifting of the toes) in the swing phase by means of an elastic element.

It can be seen from these examples that the important controls of an artificial foot during standing or walking can also be undertaken appropriately as a function of the floor inclination or heel height, with it already sufficing to control the movement resistance by means of the hydraulic cylinder.

The following modes of operation are implemented in the case of one exemplary embodiment for detecting the movement states of the foot prosthesis and the control which results therefrom:

Distinguishing Standing-Walking

Walking and standing are distinguished according to the following criteria:
 1. Detecting a swing phase
    A swing phase is detected by virtue of the fact that the ankle moment is approximately zero since the foot is unloaded during the swing phase.
    The absolute angle of the foot part 10 exceeds a threshold for standing, which can be individually defined. Furthermore, the absolute angular velocity exceeds a defined threshold.

2. Detecting a heel impact in the swung-forward state
A negative ankle movement (plantar flexion) is detected. The absolute-angle signal corresponds to that of a swung-forward foot compared to a threshold for standing which has been individually defined.
Optionally, a plantar flexion during the heel impact can be indicated by means of the ankle angular velocity.
3. Return to standing
After a detected heel impact, the absolute angle of the foot part 10 remains within a threshold value for standing which has been individually defined. As an alternative or in addition to this, an active reversal of the movement direction from dorsal to plantar in the central stance phase can be detected as a criterion for standing.
If standing has been detected, the control valves 27, 28 are set such that this results in stops in the ventral and dorsal direction at a narrow angle (neutral position location). For the gait cycle, the stop is shifted in the dorsal direction and the damping properties for the plantar flexion and dorsiflexion are set as a function of the step length.

Distinguishing Plane-Ramp

The absolute angle measured at the beginning of the central stance phase in the gait cycle, that is to say after the entire foot has impacted on the ground, is greater than or less than a value range of the absolute angle which was defined for walking in the plane.

In accordance with the determined inclination of the ramp, the dorsal stop is changed and the damping properties during plantar flexion and dorsiflexion are set as a function of the absolute angle and the predicted step length.

Detecting Backward Motion

Backward motion is detected by detecting the back-swing phase and by detecting a forefoot impact in the backwardly extended state.

1. Detecting a back-swing phase
In the case of a measured ankle moment of approximately zero, the absolute angle signal corresponds to a backwardly-extended foot (retroversion) compared to standing, and the absolute angular velocity exceeds a defined threshold.
2. Detecting a forefoot impact in the backwardly extended state
A greater positive ankle moment is measured.
Depending on the measured values, the stop is adjusted in the dorsal direction and the damping properties in plantar flexion and dorsiflexion are set as a function of the absolute angle during the forefoot impact.

Adaptation to Different Heel Heights

The heel height is preferably determined by reading the absolute-angle signal when a trigger signal is initiated manually. The neutral point for the control valves 27, 28 is set proportionally to the absolute angle.

As an alternative to this, the heel height from a ramp inclination can be determined in the case of an artificial foot with a forefoot part 15 attached in a hinged fashion, by virtue of the fact that the angle of the forefoot part 15 is measured in relation to the main foot part 10. This is an additional option within the scope of the present invention.

Standing on Inclined Ground

In the case of a reversal of the movement direction from plantar to dorsal, the absolute angle is measured when the ankle moment undergoes a zero crossing. Accordingly, the dorsal stop for controlling the hydraulic cylinder 17 with the control valves 27, 28 is adjusted as a function of the ground inclination.

Detecting Walking on Stairs

The vertical distance travelled and the horizontal distance travelled by the main foot part 10 can be determined if the absolute-angle sensor 20 comprises two acceleration sensors for acceleration components in the direction of plumb line and the acceleration components can be output separately. The distances traveled are determined by integrating twice over the corresponding acceleration components. In these cases, walking up and down stairs can be distinguished and the stops for the damping properties during plantar flexion and dorsiflexion can be set appropriately.

The accelerations can be used in a similar manner to set walking at different walking velocities by correspondingly changing the stops in the dorsal direction and the damping properties during plantar flexion and dorsiflexion.

The invention claimed is:

1. Passive orthopedic aid being a foot prosthesis or foot orthosis, comprising:
a first part and a second part both rotatably connected to each other by a swivel joint, so as to allow a rotation movement between the first part and the second part having a certain movement resistance,
a sensor arrangement for measuring parameters that provide indications of instantaneous operation requirements of the passive orthopedic aid,
a controller connected to the sensor arrangement including a processor arrangement configured to determine operation requirements and to generate control signals corresponding to the determined operation requirements,
a controllable hydraulic damping arrangement configured to modify the certain movement resistance of the rotation movement between the first part and the second part and being controlled by the control signals of said controller, wherein
the controllable hydraulic damping arrangement has hydraulic chambers,
the hydraulic chambers are connected to permit flow of hydraulic fluid between the hydraulic chambers in a first flow direction or a second flow direction opposite the first flow direction,
flow resistances between the hydraulic chambers are controlled by the controller using controllable valves for adjusting the certain movement resistance, including different flow resistances during a gait cycle,
the sensor arrangement includes an ankle moment sensor configured to detect where an ankle moment crosses zero during said gait cycle,
the processor arrangement is configured to determine a current neutral point position for each gait cycle from the zero crossing of the ankle moment detected by the ankle moment sensor, and
the processor is configured to take into account the current neutral point position determined by the processor arrangement from the zero crossing of the ankle moment for generating the control signals which control the flow resistances between the hydraulic chambers.

2. Passive orthopedic aid according to claim 1, wherein at least one flow resistance of the different flow resistances between the hydraulic chambers is increasable such that the swivel joint can be locked in any desired position.

3. Passive orthopedic aid according to claim 2, wherein the locked position corresponds to the neutral point position.

4. Passive orthopedic aid according to claim 1, wherein the neutral point position is determinable as a function of a ground inclination.

5. Passive orthopedic aid according to claim 4, wherein the neutral point position is determinable as a function of a current height of a heel of a shoe that is used with the orthopedic aid.

6. Passive orthopedic aid according to claim 1, wherein the first part and the second part are mostly rigid, and wherein at least most of said rotation movement within said gait cycle is controlled by control of the different flow resistances, without being influenced by material elasticities.

7. Passive orthopedic aid according to claim 1, wherein the swivel joint is an ankle joint.

8. A passive orthopedic aid that is a foot prosthesis or foot orthosis, comprising:
  a first part and a second part;
  a swivel joint connecting and allowing a rotation movement between the first part and the second part;
  a controllable hydraulic damping arrangement having hydraulic chambers connected to passively permit flow of hydraulic fluid between the hydraulic chambers in a first flow direction or a second flow direction opposite the first flow direction, wherein the controllable hydraulic damping arrangement is configured to modify a movement resistance of the rotation movement between the first part and the second part by adjusting flow resistances between the hydraulic chambers during a gait cycle using controllable valves;
  a sensor arrangement including an ankle moment sensor measuring an ankle moment; and a controller connected to the sensor arrangement including a processor arrangement configured to determine operation requirements,
  wherein the processor arrangement is configured to:
    determine where the ankle moment measured by the ankle moment sensor crosses zero during said gait cycle,
    determine a current neutral point position for said gait cycle from the determined zero crossing of the ankle moment, and
  a controller connected to the sensor arrangement including a processor arrangement configured to determine operation requirements and
    generate control signals which control the flow resistances through the controlled valves between the hydraulic chambers of the hydraulic damping arrangement taking into account the current neutral point position determined from the determined zero crossing of the ankle moment.

9. The passive orthopedic aid according to claim 8, wherein the hydraulic chambers are synchronously changing hydraulic chambers.

* * * * *